United States Patent [19]
Martin

[11] Patent Number: 5,876,637
[45] Date of Patent: Mar. 2, 1999

[54] LUMINESCENT COPPER ALUMINUM HALIDE MATERIALS

[75] Inventor: James D. Martin, Apex, N.C.

[73] Assignee: North Carolina State University, Raleigh, N.C.

[21] Appl. No.: 699,862

[22] Filed: Aug. 20, 1996

[51] Int. Cl.⁶ .............................. G02B 5/20; C09K 11/08; C01B 9/00
[52] U.S. Cl. ................................ 252/584; 252/301.4 H; 423/463
[58] Field of Search .......................... 252/584, 301.4 H; 423/463

[56] References Cited

U.S. PATENT DOCUMENTS

| | | | |
|---|---|---|---|
| 3,440,296 | 4/1969 | Walker | 423/463 |
| 3,702,828 | 11/1972 | Hoffman | 252/301.4 R |
| 3,766,080 | 10/1973 | Swinehart et al. | 252/300 |
| 4,099,984 | 7/1978 | Christenson et al. | 134/42 |
| 4,100,183 | 7/1978 | Christenson | 423/463 |
| 4,102,802 | 7/1978 | Johnson et al. | 252/184 |
| 4,129,519 | 12/1978 | Matsuzawa | 252/301.4 H |
| 4,141,960 | 2/1979 | Long et al. | 423/463 |
| 4,997,597 | 3/1991 | Clough et al. | 252/646 |
| 5,100,587 | 3/1992 | Clough et al. | 252/646 |

FOREIGN PATENT DOCUMENTS 84-69206 of 1996 Japan .

OTHER PUBLICATIONS

Yamada et al., Chemical Abstracts 122: 278629, Abstract of J. Mol. Struct., No. 345, pp. 219–227, (1995).

*Primary Examiner*—Philip Tucker
*Attorney, Agent, or Firm*—Myers Bigel Sibley & Sajovec, P.A.

[57] ABSTRACT

A system for displaying luminescence comprises a crystalline structure comprising a compound having the formula:

$$\alpha\text{-CuAlX}_4$$

wherein the compound has lattice parameters a=b ranging from 5.430(1) Å to 5.751(3) Å; c ranging from 10.069(1) Å to 10.570(4) Å; and X is selected from the group consisting of chlorine, bromine, and a mixture thereof. The crystalline structure may also include a compound of the formula:

$$\beta\text{-CUAlCl}_4$$

wherein the compound has lattice parameters a=7.635(2) Å, b=12.842(2) Å, and c=6.127(1) Å. The system also includes an excitation source which transmits energy to the crystalline structure such that the crystalline structure displays luminescence. The crystalline structure is also useful in a gas sensor application since the luminescence of the crystalline structure is capable of being quenched in the presence of gaseous material.

24 Claims, 2 Drawing Sheets

5,876,637

LUMINESCENT COPPER ALUMINUM HALIDE MATERIALS

FIELD OF THE INVENTION

The present invention relates to copper aluminum halide materials having luminescent properties. More particularly, the invention relates to copper aluminum halide materials whose luminescent properties are quenched in the presence of gaseous substances.

BACKGROUND OF THE INVENTION

Separation of potentially harmful environmental pollutants, specifically gases, is increasingly important. As an example, carbon monoxide is a poisonous gas produced as a by-product during the combustion of fossil fuels. With the growth of fossil fuel consumption, there remains an ever increasing need for carbon monoxide separation.

Recent efforts have focused on the preparation of materials which adsorb or complex with carbon monoxide to clean the gas stream containing that compound. For example, Japanese Patent No. 84-69206; and U.S. Pat. No. 4,099,984 to Christianson et al. proposes various metal halide materials which complex or adsorb with CO. Nonetheless, in spite of these efforts, there remains a need to monitor the actual adsorption or complexing of the carbon monoxide.

Monitoring of CO has traditionally been difficult due to the odorless and colorless nature of the gas. It would be especially desirable to signal when potentially dangerous levels of the gas are present. Moreover, in gas separation applications, monitoring the system so as to signal when the separation of the gas is near end to allow for regeneration of the adsorbing materials for subsequent use would be advantageous.

SUMMARY OF THE INVENTION

It is therefore an object of the present invention to provide a system and method of detecting a gaseous material.

Accordingly, a first aspect of the present invention provides a system which comprises a crystalline material and an excitation source which transmits energy to the crystalline structure. As a result, luminescence is displayed. Advantageously, when the system is exposed to a gaseous material such as carbon monoxide, it is adsorbed by the crystalline structure to quench the luminescence. Thus, monitoring of the presence of gaseous material is made possible.

Specifically, the crystalline structure comprises a compound having the formula:

α-CuAlX$_4$ wherein said compound has lattice parameters a=b ranging from 5.430(1) Å to 5.751(3) Å; and c ranging from 10.069 (1) Å to 10.570(4) Å; α=β=γ=90°; and X is selected from the group consisting of chlorine, bromine, and a mixture thereof. Preferably, X is chlorine or bromine, most preferably, chlorine.

The excitation source is preferably UV light. As a result, the crystalline structure may display luminescence having a wavelength of about 480 nm.

The system which comprises the crystalline structure and excitation source can be present in or incorporated into many devices. Such devices include a video display screen, an LED, a solid state laser, a lamp, an imaging plate, and a fluorescent marker or tag.

As indicated above, the system also may be fabricated as a sensor such that gaseous material may be absorbed by the system. Preferably, the gaseous material is selected from carbon monoxide and ethylene. In one embodiment, the system may be present in a dynamic flow gas separation sensor. In another embodiment, the system may be present in a static gas sensor.

A second aspect of the present invention is a crystalline structure having the formula:

β-CuAlX$_4$ wherein said compound is in the form of a crystalline structure and has lattice parameters a ranging from 7.635(2) Å to 7.871(3) Å; b ranging from 12.842(2) Å to 13.199 Å; c ranging from 6.127(1) Å to 6.292(3) Å; α=90.0°; β=90.0°; and γ=90.0°; and wherein X is selected from the group consisting of chlorine, bromine, and mixtures thereof.

A third aspect of the present invention is a system which comprises a crystalline material and an excitation source as described above wherein the crystalline structure has the formula β-CuAlCl$_4$ as defined above.

BRIEF DESCRIPTION OF THE DRAWINGS

In the drawings which form a portion of the disclosure of the invention.

DETAILED DESCRIPTION OF THE INVENTION

Figure 1:
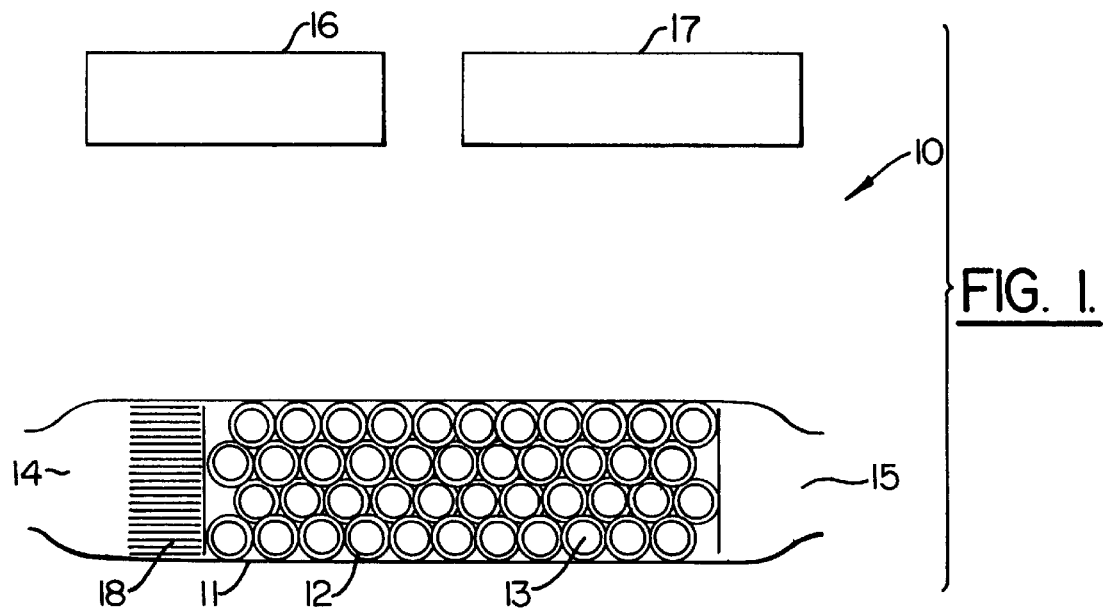
FIG. 1 is a schematic view of a dynamic gas flow sensor which detects the presence of a gaseous material in accordance with the invention.

The present invention will now be described more fully hereinafter, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art. In the drawings, like numbers refer to like elements throughout.

The present invention relates to a system for displaying luminescence. The system includes a crystalline structure which comprises a compound having the formula:

α-CuAlX$_4$

The compound crystallizes in the tetragonal space group P-42c and has lattice parameters a=b ranging from 5.430(1) Å to 5.751(3) Å; and c ranging from 10.069(1) Å to 10.570(4) Å. In the above formula, X is selected from the group consisting of chlorine, bromine, and mixtures thereof. The system also includes an excitation source which transmits energy to the crystalline structure such that the crystalline structure displays luminescence.

The crystalline structure of the formula:

α-CuAlCl$_4$ has previously been reported in Z. Naturforsch, 1982, 37b, p. 1129. The above crystalline structure exhibits a three-dimensional framework of corner sharing CuCl$_4$ and AlCl$_4$ tetrahedra.

As indicated, the halide group X may be chlorine, bromine, or a mixture of the two. When X is chlorine, the lattice parameters are as follows: a=b is 5.430(1) Å, and c is 10.069(1) Å. When X is bromine, a=b is 5.751(3) Å, and c is 10.570(4) Å. Additionally as illustrated below, the following parameters represent various chlorine and bromine mixtures of the α-structure.

| Formula | lattice parameter value |
|---|---|
| α-CuAlBrCl$_3$ | a = 5.5208(11) Å |
| | b = 5.5208(11) Å |
| | c = 10.1970(52) Å |
| α-CuAlBr$_2$Cl$_2$ | a = 5.6069(14) Å |
| | b = 5.6069(14) Å |
| | c = 10.3151(32) Å |
| α-CuAlBr$_3$Cl | a = 5.6778(8) Å |
| | b = 5.6778(8) Å |
| | c = 10.4687(25) Å |

The following parameters (bond lengths, non-bonded contacts, and bond angles) listed in Table 1 below have been determined by conventional techniques as representative of the structures of CuAlCl$_4$ and CuAlBr$_4$.

TABLE 1

| | CuAlCl$_4$ | CuAlBr$_4$ |
|---|---|---|
| Bond Lengths (Å) | | |
| Cu-X | 2.3605(8) | 2.4797(6) |
| Al-X | 2.1449(6) | 2.3059(6) |
| Non-bonded Contacts (Å) | | |
| X-X (Cu tetrahedron) | 3.930(2) | 4.158(1) |
| | 3.816(1) | 3.994(1) |
| X-X (Al tetrahedron) | 3.528(2) | 3.809(1) |
| | 3.525(1) | 3.793(1) |
| | 3.454(1) | 3.693(1) |
| X-X$_1$ | 4,168(2) | 4.300(1) |
| | 3.789(2) | 3.947(1) |
| | 3.745(1) | 3.893(1) |
| X-X$_2$ | 3.865(2) | 4.052(1) |
| X-X$_3$ | 3.791(2) | 3.963(1) |
| Bond Angles | | |
| X-Cu-X | 112.72(3) | 113.96(2) |
| | 107.87(3) | 107.27(2) |
| X-Al-X | 110.53(4) | 111.37(2) |
| | 110.63(3) | 110.66(2) |
| | 107.28(3) | 106.42(2) |

The crystalline structure α-CuAlX$_4$ can be made in accordance with known methods and techniques. It should be noted that starting materials and products tend to be moisture sensitive. Thus, it is preferable to carry out all manipulations in an atmosphere of dry nitrogen. Starting materials CuX and AlX$_3$ wherein X is defined herein, can be mechanically combined in appropriate proportions to form the above crystalline structure. For example, the crystalline structure can be synthesized by grinding the two starting materials with a mortar and pestle. Additionally, the CuX and AlX$_3$ materials can be combined and melted in a sealed pyrex or fused silica ampule, preferably at a temperature of about 250° C. Slow cooling of the melt (about 25° C./hr) to room temperature (about 25° C.) yields crystalline α-CUAlX$_4$. Crystalline α-CuAlX$_4$ can also be grown by slow evaporation of a benzene solution of CuX and AlX$_3$.

In accordance with the invention, the system includes an excitation source which transmits energy to the crystalline structure such that the structure displays luminescence. Excitation sources which may be used include, but are not limited to, UV light, a cathodic electron beam, and an electric field. UV light is the preferred excitation source and has a wavelength which typically ranges from about 200 to 400 nm, and is preferably about 254 nm. As a result, the crystalline structure displays luminescent properties capable of acting as, for example, blue, green, and red/orange phosphors. For example, when the excitation source emits energy of a wavelength of about 250 nm, the crystalline structure displays blue fluorescence having a wavelength of about 480 nm. Moreover, when the excitation source emits energy of a wavelength of about 365 nm, the crystalline structure of aluminum rich samples displays red/orange fluorescence having a wavelength of about 650 nm.

Advantageously, the system of the invention can be incorporated into a number of devices so as to display luminescence by fabrication techniques that are either known or apparent to those skilled in the art. The system can be used in various flat panel displays. Examples of specific devices include, but are not limited to, a video display screen, an LED, a solid state laser, a lamp, an imaging plate, and a fluorescent marker or tag. For the purposes of the invention, LEDs ("light emitting diodes") are to be broadly interpreted and may be incorporated into devices not limited to, light sources, readouts, signal lamps, sensors, and optical signalings.

As an advantageous feature of the invention, the crystalline materials are capable of absorbing various gaseous materials which, in turn, quench the luminescence of the crystalline materials. In particular, the intensity of the luminescence is observed to be inversely proportional to the amount of gaseous material absorbed. When the crystalline material is used as a gas sensor, one is able to monitor the amount of gas being absorbed by the crystalline material. For example, when used in a gas separations reactor, substantially complete quenching of the luminescence may signal when to terminate the gas mixture feed to the reactor. Moreover, the quenching of the luminescence is reversible: when the gas is evacuated from the crystalline material, the crystalline material again displays luminescence.

A number of gaseous materials may be used in the invention. Specific examples include carbon monoxide, along with nitric oxide, ethylene, hydrogen/carbon monoxide mixtures, and any mixture of the above. Preferably, the gaseous material is selected from carbon monoxide and ethylene. Carbon monoxide is most preferred for use with the invention. The gaseous material(s) may be provided in essentially pure form or in a mixture with other gases, as in an exhaust gas, household air, or coal-gasification products.

Various devices may employ the crystalline structure to detect and/or separate gaseous materials. As an example, FIG. 1 represents a dynamic flow gas separation sensor represented as 10. The sensor 10 is made up primarily of a tube 11, preferably of quartz, which contains the crystalline material therein. The crystalline material is usually present in the form of a film or layer 12 which is deposited on a substrate 13. In FIG. 1, a plurality of glass beads make up the substrate. Inlet and outlet ports 14 and 15 respectively allow the gaseous material to be transported through the sensor. An excitation source 16 is employed to transmit energy to the crystalline material. The luminescence of the material is measured by a conventional detection source 17.

The sensor 10 allows for the detection of the presence of the gaseous substance adsorbed by the crystalline material. Gaseous material is introduced to the sensor 10 through inlet port 14 under various pressure and temperature conditions. At this time, the excitation source 16 is employed such that the crystalline material displays luminescence. A portion of the gaseous material, such as carbon monoxide for example, contacts the film or layer 12 of crystalline material so as to be adsorbed by the crystalline material. The remaining portion of the gaseous material exits through outlet port 15. During this time, device 17 monitors the change in luminescence of the material so as to detect the presence of the gaseous material. The monitoring device 17 may be used in conjunction with a suitable registering device (not shown), to allow for one to obtain a record of the change in luminescence.

The crystalline material of the invention may be sensitive to moisture so as to potentially become less effective. Accordingly, a hydrophobic matrix material illustrated by 18 may be utilized to capture or repel moisture present in the gaseous material as it enters quartz tube 11.

Figure 2:
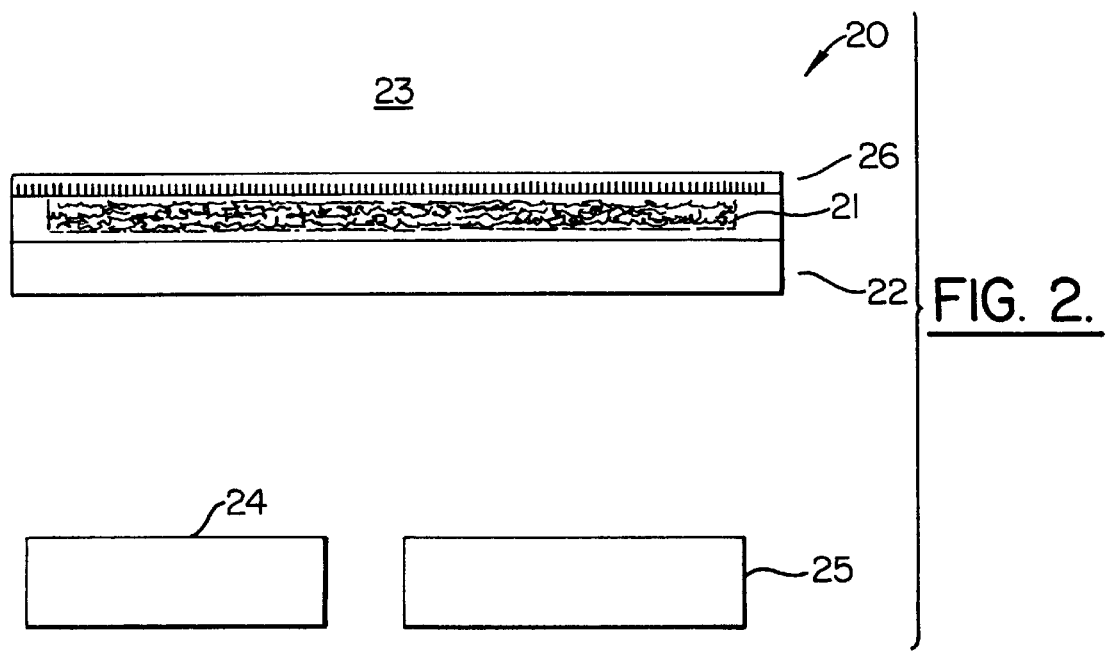
FIG. 2 is a schematic view of a static gas sensor which detects the presence of a gaseous material in accordance with the invention.

The detection of the presence of the gaseous substance may also be carried out in a static gas sensor 20 illustrated in FIG. 2. In this instance, the crystalline material is present as a film or layer 21 on substrate 22, preferably made of quartz. Alternatively, the substrate 22 could be an optical fiber. A reversible gas exchange 23 is present adjacent to the static sensor 20 and serves as a sink and source of various gaseous materials such as carbon monoxide. Similar to the dynamic sensor 10, an excitation source 24 is employed to transfer energy and impart luminescence to the crystalline material 21. As the gaseous material contacts the crystalline material 21, the monitoring device 25 detects a change in the luminescence of the crystalline material corresponding to the gaseous material being absorbed. A hydrophobic barrier 26 is preferably present between the crystalline material 21 and the gas exchange 23 to prevent moisture from contacting the crystalline material 21.

The sensing devices illustrated in FIGS. 1 and 2 may be employed in a variety of applications. For example, the dynamic flow device depicted in FIG. 1 may be used as a sensing device to signal the point of saturation and thus the need for regeneration in a gas separation system, or the presence of potentially unsafe levels of CO in gas streams in industrial facilities. The static sensor of FIG. 2 may be employed, for example, as a sensor which measures potentially unsafe CO levels in household and other interior environments or be attached to the end of a fiber for remote sensing.

The present invention also is directed to a compound of the formula:

$$\beta\text{-CuAlX}_4$$

wherein the compound is in the form of a crystalline structure and X is selected from the group consisting of chlorine, bromine, and a mixture of bromine and chlorine. Preferably X is chlorine, with the crystalline structure having lattice parameters a=7.635(2) Å; b=12.842(2) Å; c=6.127(1) Å; $\alpha$=90.0°; $\beta$=90.0°; and $\gamma$=90.0°. Additionally as illustrated below, the following parameters represent various chlorine and bromine mixtures of the $\beta$-structure.

| Formula | lattice parameter value |
|---|---|
| $\beta$-CuAlBrCl$_3$ | a = 7.875(3) Å |
| | b = 13.162(6) Å |
| | c = 6.296(3) Å |
| $\beta$-CuAlBr$_2$Cl$_2$ | a = 7.684(4) Å |
| | b = 12.908(6) Å |
| | c = 6.152(4) Å |
| $\beta$-CuAlBr$_3$Cl | a = 7.871(3) Å |
| | b = 13.199(7) Å |
| | c = 6.292(3) Å |

The parameters were determined from single crystal and powder x-ray diffraction techniques.

The $\beta$-CuAlCl$_4$ structure exhibits a three-dimensional framework of corner sharing CUCl$_4$ and AlCl$_4$ tetrahedra. Specifically, it has been determined that the $\beta$-CuAlCl$_4$ structure crystallizes with orthorhombic Pna2$_1$ space group symmetry.

The $\beta$-CuAlCl$_4$ crystalline structure is produced by combining a melt blend of CuCl and AlCl$_3$, and thereafter rapidly quenching the molten blend into an ice bath or liquid nitrogen. Accordingly, the crystalline structure is produced. It should be emphasized that the above technique yields the $\beta$-CuAlCl$_4$ crystalline structure exclusively. Rapid quenching can be achieved by varying techniques. For example, altering the thickness of the reaction vessel can influence the quenching. Specifically, it has been found that changing the thickness of the reaction vessel walls of fused silica from 1 mm to 2 mm yields differing cooling rates. Characterization of the $\beta$-CuAlCl$_4$ structure is confirmed by conventional x-ray diffraction techniques. $\beta$-CuAlCl$_4$ can also be prepared from a benzene solution of CuCl and AlCl$_3$ by rapidly removing the solvent in a vacuum ($10^{-3}$ torr).

In accordance with the invention, the $\beta$-CuAlCl$_4$ crystalline structure has been found to display luminescent properties which may be reversibly quenched in the presence of the gaseous materials described herein. Specifically, a system containing $\beta$-CuAlCl$_4$ emits light with a wavelength of about 490 nm. As a result, the $\beta$ structure may be utilized alone or in combination with the $\alpha$-structure in, for example, any of the gas sensing or luminescent displaying devices described herein.

In accordance with the invention, it has been found that 1 mole of $\alpha$- or $\beta$-CuAlCl$_4$ is capable of absorbing about 0.5 mole of carbon monoxide. Additionally, 1 mole of $\alpha$- or $\beta$-CUAlCl$_4$ is capable of absorbing about 0.5 mole of ethylene. The rate of this absorption/quenching can thus be varied by the concentration of gas in the flow stream. A stream having a high flow rate and a low gas concentration or a stream having a low flow rate and a high gas concentration will have similar adsorption/quenching rates. The selection of the gas stream flow rates and concentrations is readily within the ability of one skilled in the art.

The foregoing examples are illustrative of the present invention, and are not to be construed as limiting thereof.

EXAMPLE 1

Synthesis of $\beta$-CuAlCl$_4$

The $\beta$-CuAlCl$_4$ structure is synthesized by first melting the compounds CuCl and AlCl$_3$ at a temperature at or above about 250° C. in a fused silicon tube with a wall thickness of less than 1 mm. Rapid quenching of the melt in a suitable medium such as an ice bath provides a quantitative yield of $\beta$-CUAlCl$_4$. Quenching of the above melt using a slightly slower cooling profile, by employing thick walled tubing or quenching in air, yields a crystalline structure which is a mixture of rectangular prism single crystals of $\beta$-CuAlCl$_4$ and microcrystalline $\alpha$-CUAlCl$_4$. Annealing a sample of $\beta$-CuAlCl$_4$ at 100° C. for at least about 12 hours causes the structure to revert to the $\alpha$-CuAlCl$_4$ structure.

EXAMPLE 2

Characterization of $\beta$-CuAlCl$_4$

Figure 3:
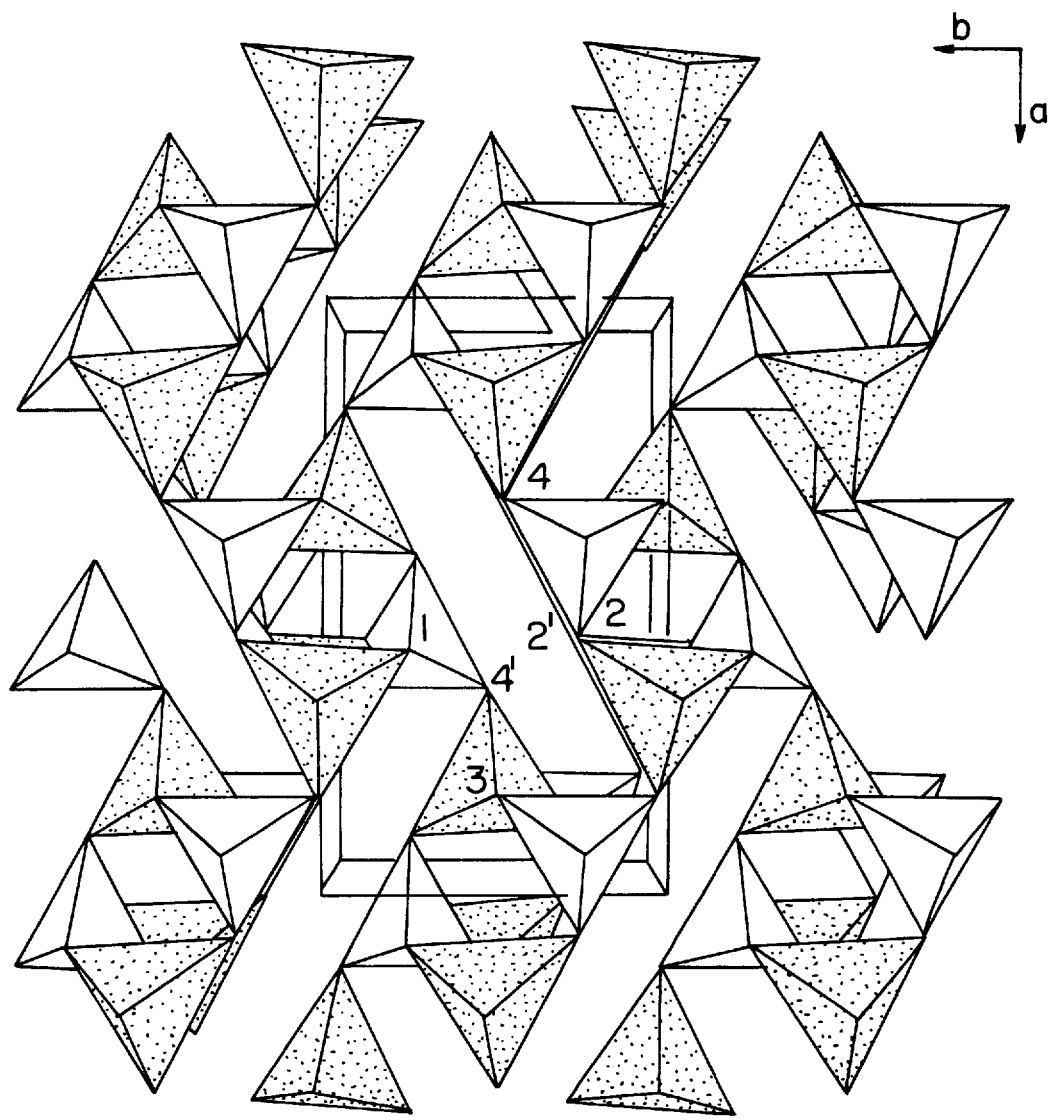
FIG. 3 is a schematic view of the crystalline structure of β-CuClAl$_4$.

The following structure and parameters of the $\beta$-CuAlCl$_4$ crystalline lattice were determined by x-ray diffraction. FIG. 3 represents the structure of the $\beta$-CuAlCl$_4$ crystalline lattice. In the figure, the numbers 1, 2, 3, and 4 refer to the various positions of Cl atoms. 2 and 2'; 3, 3', and 3"; and 4 and 4' refer to symmetrically equivalent positions. The crystalline structure contains Van der Waals channels running along the a and c axes constructed with 6-ring and 8-ring orifices, respectively. The inter-tetrahedral Cl—Cl distances were determined to range from about 3.75 Å to 4.11 Å, while the average intra-tetrahedral Cl—Cl distances were measured to be 3.50 Å and 3.85 Å for the Al and Cu tetrahedra, respectively. The 8-ring channels running along the c axis have a free diameter of 8.3 Å (Cl(4)–Cl(4)=11.71 Å) along the widest dimension, while the shortest cross-channel contact is 0.4 Å (Cl(2)–Cl(4)=3.79 Å). The height of the snaking channels running along the a axis is equivalent to the c axis lattice constant, 6.13 Å (free diameter of 2.67 Å) while the width varies from Cl(1)–Cl(3)=3.75 Å to Cl(3)–Cl(4)=4.11 Å (free diameters of 0.4 Å and 0.7 Å, respectively). The closest cross channel halide-halide contacts cut the 6-ring orifice. The smaller $AlCl_4$ tetrahedra are responsible for the varying width of the channel.

EXAMPLE 3

Luminescent Activity of α- and β-CuAlCl₄

α-CUAlCl₄ and β-CUAlCl₄ were each placed in a quartz chamber and exposed to UV light at 250 nm. Both materials display luminescence. Flushing the chamber with gaseous carbon monoxide (99 percent) causes a quenching of the luminescence of the materials. Removing the gaseous mixture from the chamber by a moderate vacuum (0.1 torr) results in the materials displaying luminescence.

In the specification, drawings and example, there have been disclosed typical preferred embodiments of the invention and, although specific terms are employed, they are used in a generic and descriptive sense only and not for purposes of limitation of the scope of the invention being set forth in the following claims.

That which is claimed is:

1. A system for displaying luminescence comprising:
   a crystalline structure comprising a compound having the formula:

α-CuAlX₄ wherein said compound has lattice parameters a=b ranging from 5.430(1) Å to 5.751(3) Å; c ranging from 10.069(1) Å to 10.570(4) Å; and X is selected from the group consisting of chlorine, bromine, and a mixture thereof; and
   an excitation source which transmits energy to the crystalline structure such that the crystalline structure displays luminescence.

2. The system according to claim 1, wherein X is chlorine and a=b=5.430(1) Å; and c=10.069(1) Å.

3. The system according to claim 1, wherein X is a mixture of chlorine and bromine.

4. The system according to claim 1, wherein said excitation source is UV light.

5. The system according to claim 4, wherein said crystalline structure displays blue luminescence having a wavelength of about 480 nm.

6. The system according to claim 1, wherein said system is present in a device selected from the group consisting of a video display screen, an LED, a solid state laser, a lamp, an imaging plate, and a fluorescent marker or tag.

7. The system according to claim 1, wherein said system further comprises a gaseous material capable of being adsorbed by said crystalline structure such that the luminescence of the compound becomes quenched.

8. The system according to claim 7, wherein said gaseous material may be selected from carbon monoxide and ethylene.

9. The system according to claim 7, wherein said system is incorporated into a dynamic flow gas separation sensor.

10. The system according to claim 7, wherein said system is incorporated into a static gas sensor.

11. The system according to claim 1, wherein said crystalline structure further comprises a compound having the formula:

β-CUAlCl₄ wherein said compound has lattice parameters a=7.635(2) Å; b=12.842(2) Å; and c=6.127(1) Å.

12. A method of detecting a gaseous material in a crystalline structure, said method comprising:
    providing a crystalline structure comprising a compound having the formula:

α-CUAlX₄ wherein said compound has lattice parameters a=b ranging from 5.430(1) Å to 5.751(3) Å; and c ranging from 10.069(1) Å to 10.570(4) Å; X is selected from the group consisting of chlorine, bromine, and a mixture thereof;
    exciting said crystalline structure with an excitation source which transmits energy to the crystalline structure such that the crystalline structure displays luminescence;
    contacting said crystalline structure with a gaseous material such that the gaseous material is adsorbed by the crystalline structure; and
    monitoring a change in the luminescence of said crystalline structure to detect the presence of the gaseous material.

13. The method according to claim 12, wherein X is chlorine and a=b=5.430(1) Å; and c=10.069(1) Å.

14. The method according to claim 12, wherein X is a mixture of chlorine and bromine.

15. The method according to claim 12, wherein the excitation source is UV light.

16. The method according to claim 12, wherein the gaseous material comprises carbon monoxide.

17. The method according to claim 12, wherein the crystalline structure is incorporated into a dynamic flow gas sensor.

18. The method according to claim 17, wherein the crystalline structure is deposited on a substrate comprising a plurality of glass beads.

19. The method according to claim 12, wherein the crystalline structure is incorporated into a static gas sensor.

20. The method according to claim 12, wherein the crystalline structure further comprises a compound having the formula:

β-CUAlCl₄ wherein said compound has lattice parameters a=7.635(2) Å, b=12.842(2) Å, and c=6.127(1) Å.

21. A compound having the formula:

β-CuAlX₄ wherein said compound is in the form of a crystalline structure and has lattice parameters a ranging from 7.635(2) Å to 7.871(3) Å; b ranging from 12.842(2) Å to 13.199(7) Å; c ranging from 6.127(1) Å to 6.292(3) Å; α=90.0°; β=90.0°; and γ=90.0°; and wherein X is selected from the group consisting of chlorine, bromine, and a mixture thereof.

22. The compound according to claim 21, wherein the crystalline structure has orthorhombic Pna2$_1$ space symmetry.

23. The compound according to claim 21, wherein the crystalline structure has inter-tetrahedral distances ranging from 3.75 Å to 4.11 Å.

24. The compound according to claim 21, wherein X is chlorine and a=7.635(2) Å, b=12.842(2) Å, and c=6.127(1) Å.

* * * * *

UNITED STATES PATENT AND TRADEMARK OFFICE
CERTIFICATE OF CORRECTION

PATENT NO.    :  5,876,637
DATED         :  March 2, 1999
INVENTOR(S)   :  James D. Martin It is certified that error appears in the above-identified patent and that said Letters Patent is hereby corrected as shown below:

Abstract [57],            "β-CUA1C1$_4$" should read --β-CuA1C1$_4$--.

Column 8, line 58, Claim 20    "β-CUA1C1$_4$" should read --β-CuA1C1$_4$--.

Signed and Sealed this

First Day of February, 2000

Attest:

Q. TODD DICKINSON

Attesting Officer    Acting Commissioner of Patents and Trademarks